United States Patent
Ikegawa

(10) Patent No.: US 8,783,364 B2
(45) Date of Patent: Jul. 22, 2014

(54) METHOD FOR PRODUCTION, SUBSTITUTION, OR MINING OF GAS HYDRATE

(75) Inventor: Yojiro Ikegawa, Chiba (JP)

(73) Assignee: Central Research Institute of Electric Power Industry, Tokyo (JP)

( * ) Notice: Subject to any disclaimer, the term of this patent is extended or adjusted under 35 U.S.C. 154(b) by 699 days.

(21) Appl. No.: 12/063,819

(22) PCT Filed: Aug. 25, 2006

(86) PCT No.: PCT/JP2006/316726
§ 371 (c)(1),
(2), (4) Date: Feb. 14, 2008

(87) PCT Pub. No.: WO2007/023943
PCT Pub. Date: Mar. 1, 2007

(65) Prior Publication Data
US 2010/0193180 A9      Aug. 5, 2010

(30) Foreign Application Priority Data
Aug. 26, 2005   (JP) .................................. 2005-245769

(51) Int. Cl.
*E21B 43/00*    (2006.01)
(52) U.S. Cl.
USPC ........ 166/371; 166/249; 166/402; 166/272.6; 299/3; 405/131; 585/15; 62/53.1
(58) Field of Classification Search
None
See application file for complete search history.

(56) References Cited

U.S. PATENT DOCUMENTS

| | | | |
|---|---|---|---|
| 5,044,164 A | | 9/1991 | Bee |
| 5,261,490 A | * | 11/1993 | Ebinuma ....................... 166/266 |
| 5,562,891 A | * | 10/1996 | Spencer et al. ............. 423/437.1 |
| 5,998,681 A | * | 12/1999 | Rojey ............................... 585/15 |
| 6,733,573 B2 | * | 5/2004 | Lyon ............................... 95/153 |
| 7,165,621 B2 | * | 1/2007 | Ayoub et al. .................. 166/369 |
| 7,222,673 B2 | * | 5/2007 | Graue et al. ................ 166/305.1 |
| 2004/0200618 A1 | * | 10/2004 | Piekenbrock .............. 166/305.1 |

FOREIGN PATENT DOCUMENTS

| | | |
|---|---|---|
| JP | 2-86840 A | 3/1990 |
| JP | 6-71161 A | 3/1994 |
| JP | 2000-61293 A | 2/2000 |
| JP | 2003-214082 A | 7/2003 |
| JP | 2004-113926 A | 4/2004 |
| JP | 2004-321952 A | 11/2004 |
| WO | WO 2006/016333 A1 | 2/2006 |

OTHER PUBLICATIONS

Kazunari Ohgaki, Kiyoteru Takano and Masato Moritoki, "Exploitation of CH4 Hydrates under the Nankai Trough in Combination with CO2 Storage", Kagaku Kogaku Ronbunshu, vol. 20, No. 1, Jan. 1994, p. 121-123.

(Continued)

*Primary Examiner* — Angela M DiTrani
(74) *Attorney, Agent, or Firm* — Notaro, Michalos & Zaccaria P.C.

(57) ABSTRACT

A gas hydrate is produced by injecting guest molecules into voids in a layer of which temperature and pressure condition allows the guest molecules to cause to form hydrate, in a form of emulsion where liquid of the guest molecules is dispersed in water as minute particles having a size of less than a size of voids, and thereby dispersing the guest molecules uniformly into the voids in the layer.

8 Claims, 11 Drawing Sheets

(56) References Cited

OTHER PUBLICATIONS

Kazunari Ohgaki, Kiyoteru Takano, Hiroyuki Sangawa, Takuya Matsubara, and Shinya Nakano, Methene Exploitation by Carbon Dioxide From Gas Hydrates, Journal of Chemical Engineering of Japan, vol. 29, No. 3, p. 478-483.

Dan S. Golomb, "Carbon Dioxide/Limestone/Water Emulsion for Ocean and Geologic Sequestration of CO2", Greenhouse gas Control Technologies, vol. I, p. 683-688.

* cited by examiner

METHOD FOR PRODUCTION, SUBSTITUTION, OR MINING OF GAS HYDRATE

FIELD OF THE INVENTION

This invention relates to methods for production, substitution, and mining of gas hydrate. More particularly, this invention relates to a method for fixation of carbon dioxide ($CO_2$), and a method useful for mining of methane ($CH_4$) hydrate by substitution utilizing the fixation.

BACKGROUND

In order to prevent the global warming due to the release of enormous amounts of $CO_2$, it has been studied to fixate $CO_2$ to the submarine layer, lake bottom layer, permafrost, or the like by hydrating $CO_2$. Meanwhile, vast amounts of $CH_4$ hydrate lie under submarine layer or the like have been attracted as a new energy source, and thus the mining of $CH_4$ hydrate has been studied. Further, it has been also studied to mine $CH_4$ while fixating $CO_2$ by substituting $CH_4$ molecules in $CH_4$ hydrate to $CO_2$ molecules.

For instance, a research paper the prior art discloses the substitution of $CH_4$ molecules in $CH_4$ hydrate to $CO_2$ molecules (Kazunari Ohgaki, Kiyomitsu Takano, Masairi Moritoki, "Utilization of CH.sub.4 hydrate and reservation of $CO_2$ in Nankai trough", Collection of Chemical Engineering Essay, Japan, 20 (1), 1994.01, pp. 121-123). In this research paper, it is discussed, thermodynamically, that methane as guest molecules in hydrate lattice is substituted to carbon dioxide without decomposing the hydrate lattice under the mixture state of $CH_4$ gas, carbon dioxide, water, $CH_4$ hydrate and carbon dioxide hydrate.

Further, a method for fixation of carbon dioxide has been proposed, wherein carbon dioxide is introduced to the underground $CH_4$ hydrate layer in order to substitute methane with carbon dioxide and fixate the carbon dioxide as carbon dioxide hydrate to the hydrate layer, and extract natural gas to the Earth's surface (Japanese Patent Publication HEI 6-71161). Since a condition where $CH_4$ hydrate exists stably also functions as a condition where carbon dioxide hydrate exists stably, the carbon dioxide hydrate can be produced by injecting gaseous or liquid carbon dioxide to the $CH_4$ hydrate layer through a penetrating injection pipe, while by the exothermal reaction at this production the $CH_4$ hydrate can be decomposed. Then, the methane gas is recovered to the ground through a separate exhaust pipe.

Incidentally, as a method for mining of gas hydrate, it has been proposed to emit a high speed jet flow to gas hydrate layer through a mining pipe which was impacted to the layer having the gas hydrate layer, in order to cut and break the gas hydrate and recover it as a gas including mixture fluid to the ground, while filling cavities in the layer which are created by the recovery of gas hydrate with the composition of the high speed jet flow (Japanese Patent Publication 2003-214082). As the composition of the high speed jet flow, a minute grain material which includes slime, cement type hardener, and/or industrial by-product such as blast furnace slag in slurry which is prepared by kneading water and silt, cohesive soil or the like is used.

SUMMARY OF THE INVENTION

The method for mining of the gas hydrate disclosed in, Japanese Patent Publication 2003-214082 however, is useless for fixating $CO_2$, because in the method the gas hydrate is merely recovered by cutting and breaking it in the layer. In addition, most of the layer as targets for mining of gas hydrate are ocean sedimentary layer where solid phases such as sand particles are connected to each other by the presence of $CH_4$ hydrate. Therefore, although the cavities which have been created after the mining are filled with the composition of the high speed jet flow, there is a fear of causing caving or landslide of the layer around the region cut and broken by the high speed jet flow, or causing cracks which is followed by embrittlement or destruction of the layer around the region cut and broken by the high speed jet flow before the fluidity of the composition of the high speed jet flow settles and the composition fixes. Thereby, $CH_4$ hydrate may come to the surface and be dissolved naturally. Therefore, the situation that the effluence of $CH_4$ gas to the ground can not be controlled may occur. Further, the substitution of gas hydrate with the minute grain material—which includes slime, cement type hardener, and/or industrial by-product such as blast furnace slag in slurry, which is prepared by kneading water and silt, cohesive soil or the like—may bring the fear of additional environmental pollution.

According to the method for fixation of carbon dioxide of (Japanese Patent Publication HEI 6-71161), since liquid $CO_2$ of almost 100% concentration is injected without mixing with water, the area of the interface between the liquid $CO_2$ and water where the hydrate producing reaction occurs is restricted and is very small, and thus there is a problem that the reaction is slow. In addition, although the ratio of water and $CO_2$ is important for the $CO_2$ hydrate producing reaction, it is hardly possible to maintain the ratio of water and $CO_2$ uniformly in the void of the layer when injecting the liquid $CO_2$ of almost 100% concentration into the layer. Therefore, it is very difficult to fixate a large amount of $CO_2$ as $CO_2$ hydrate, and it is also difficult to substitute it efficiently with a large amount of methane. Thus, the method is impractical when the fixation of a large amount of $CO_2$ at once is demanded. Further, since the ocean sedimentary layer where the $CH_4$ hydrate exists is unconsolidated one, when a large amount of liquid $CO_2$ is injected there, the liquid $CO_2$ will come to rise by buoyancy in the event that the reaction rate is slow. This is because the specific gravity of liquid $CO_2$ is lighter than that of seawater. Thus, there is a fear that the leak of liquid $CO_2$ to the ocean bottom before the $CO_2$ hydrate is produced. Furthermore, since it is difficult to predict where and how the interface between the liquid $CO_2$ and water is moved to the void in layer, it becomes difficult to predict the distribution of temperature rising of the layer due to the heat generation on the production of $CO_2$ hydrate, and to control the temperature of the layer so as to create efficiently the decomposition of $CH_4$ hydrate. Thus, there is a problem that the control of production of gas hydrate and the control of decomposition of gas hydrate are difficult.

In the case of low temperature and high pressure environment where $CO_2$ hydrate is produced, however, $CO_2$ hydrate can be produced at higher temperature and lower pressure side as compared with $CH_4$. Thus, it is the environment where $CO_2$ hydrate is retained stably as is the case with $CH_4$ hydrate, and which can fixate $CO_2$ hydrate. Therefore, in order to put the technique for fixating $CO_2$ by hydration and the technique for mining of $CH_4$ hydrate by substituting $CH_4$ hydrate with $CO_2$ hydrate to practical use, it is desired to accelerate the production rate of $CO_2$ hydrate.

It is an object of the present invention to provide to methods for production, substitution, and mining of gas hydrate, which can accelerate production rate of the gas hydrate.

The method for production of gas hydrate according to the present invention for attaining such an objective includes the steps of injecting guest molecules in a form of emulsion, wherein liquid of the guest molecules is dispersed in water as minute particles having a size of less than a size of voids in a layer, into the voids in the layer; wherein the temperature and pressure conditions of the layer allow the guest molecules to form hydrate.

The ratio of the liquid minute particle of guest molecules and water as dispersing medium, which constitute the emulsion, is not particularly limited to a certain value. Although it is preferable that the ratio is adjusted to a value suitable for producing hydrate, it is possible in some cases that the ratio of the liquid of guest molecules and water is varied in order to control the heating value per unit volume of emulsion. Further, it is also possible that the size of the liquid minute particles of guest molecules in emulsion is varied in order to control the production rate of hydrate. These controls are useful for preventing the rise in temperature of the layer associated with the production of gas hydrate from reaching a temperature of not producing the hydrate or a temperature at which the hydrate becomes unstable.

As the guest molecules in the method for production of the gas hydrate according to the present invention, any molecules capable of producing hydrate can be utilized. Among them, $CO_2$ is particularly desirable.

The method for substitution of gas hydrate according to the present invention includes the steps of injecting second guest molecules in a form of emulsion, wherein liquid of the second guest molecules is dispersed in water as minute particles having a size of less than a size of voids in a layer, into the voids in the layer in which hydrate of first guest molecules exists; wherein the second guest molecules are molecules which form hydrate under high temperature and low pressure rather that the first guest molecules; and thereby the hydrate of the first guest molecules is decomposed by heat which is generated when the hydrate of the second guest molecules is produced.

In this substitution method of gas hydrate, as is the case with the production method of gas hydrate mentioned above, the mixing ratio of the liquid of the second guest molecules and water in the emulsion may be varied in order to control the heating value per unit volume of emulsion. Further, the size of the liquid minute particles of second guest molecules in emulsion may also be varied in order to control the production rate of hydrate.

In addition, in the method for substitution of gas hydrate according to the present invention, it is preferable to use $CH_4$ as the first guest molecules, and $CO_2$ as the second guest molecules, respectively.

The method for mining of gas hydrate according to the present invention includes the steps of injecting $CO_2$ in a form of emulsion, wherein liquid $CO_2$ is dispersed in water as minute particles having a size of less than the size of voids in a $CH_4$ hydrate layer, into the voids in the $CH_4$ hydrate layer; wherein the emulsion is used as a heating agent for decomposing the $CH_4$ hydrate which exists in the voids.

Further, the method for mining of gas hydrate according to the present invention includes of the steps of forming a seal layer of $CO_2$ hydrate by injecting $CO_2$ in a form of emulsion, wherein liquid $CO_2$ is dispersed in water as minute particles having a size of less than the size of voids in a layer, into the voids in the layer, wherein the layer is rested on a $CH_4$ hydrate layer and is under the temperature and pressure condition which $CO_2$ forms hydrate; and injecting the emulsion into voids in the $CH_4$ hydrate layer; whereby $CO_2$ hydrate is produced in the voids in the $CH_4$ hydrate layer while $CH_4$ hydrate existed in the voids in the $CH_4$ hydrate layer is decomposed by heat of reaction in the $CO_2$ hydrate production, and the $CH_4$ hydrate is replaced with the $CO_2$ hydrate while recovering $CH_4$ gas.

Alternatively, the method for mining of gas hydrate according to the present invention includes the steps of forming a seal layer of $CO_2$ hydrate by injecting $CO_2$ in a form of emulsion, wherein liquid $CO_2$ is dispersed in water as minute particles having a size of less than a size of voids in a first layer, into the voids in the first layer, wherein the first layer is rested on a $CH_4$ hydrate layer and is under the temperature and pressure condition which $CO_2$ forms hydrate; injecting the emulsion into voids in a second layer, wherein the second layer is rested under the $CH_4$ hydrate layer, and thereby $CO_2$ hydrate is produced in the voids in the second layer while $CH_4$ hydrate existed in the voids in the $CH_4$ hydrate layer is decomposed from a lower side of the $CH_4$ hydrate layer by raising the temperature of the second layer using heat of reaction in the $CO_2$ hydrate production; recovering $CO_2$ gas to the ground by collecting the $CH_4$ gas using the seal layer; and restoring the strength of the $CH_4$ hydrate layer after mining of the $CH_4$ hydrate by injecting the emulsion into the void in the $CH_4$ hydrate layer after mining of the $CH_4$ hydrate and forming the $CO_2$ hydrate therein.

In accordance with the method for production of gas hydrate of the present invention—since the liquid of the guest molecules which is injected into the layer is in the emulsion state where the liquid of guest molecules is dispersed in water as particles having a size of less than the size of the voids in the layer—like water, the liquid of the guest molecules can enter into the void easily without disturbance while displacing water or seawater filled in the void in the layer from the void, or can disperse in the water or seawater. Thus, it can be distributed uniformly in the layer while maintaining the emulsion state where the minute particles of the guest molecules are admixed with the seawater. In addition, since the liquid of guest molecules is made into the emulsion state in advance of its injection into the layer, it is possible to disperse water and the guest molecules with a ratio suitable for the production of hydrate. Thus, it is possible to produce the hydrate uniformly and efficiently.

Further, since the contacting area between the liquid of guest molecules and water can be enlarged dramatically by preparing the minute particles, it is possible to accelerate the reaction rate and thus it is possible to accelerate the production of hydrate. In addition, since the hydrate can be produced quickly, it is possible to fixate a large amount of guest molecules into the layer. Furthermore, since the time required for the production of the hydrate can be shortened and the hydrate can be produced quickly, it is possible to repress the migration and diffusion of the liquid of the guest molecules. Wherein the migration and diffusion are caused by the flow of groundwater or the buoyancy of the liquid.

Further, in accordance with the method for production of gas hydrate of the present invention, it is possible to control the temperature of the layer to the temperature at which the gas hydrate can be produced, when the mixing ratio of the liquid of the guest molecules and water is varied so as to control the heating value per unit volume of emulsion, or when the temperature of water as the dispersion medium is varied so as to change the temperature of the emulsion in itself. Thus, there is no risk that the hydrate becomes unstable due to the temperature rising of the layer associated with the production of gas hydrate. There is thus no need for preparing any temperature-reducing mechanisms.

Further, in accordance with the method for production of gas hydrate of the present invention, it is possible to control the production rate of the hydrate, when the specific surface area of the minute particles of the liquid of the guest molecules in the emulsion is varied by varying the size of the minute particle. Therefore, by merely regulating the size of the minute particles of the liquid of the guest molecules, it is possible to control the production rate of the hydrate.

In addition, in the method for production of gas hydrate of the present invention, it is also possible to fixate a great amount of $CO_2$—which is the cause of global warming—in the layer, when $CO_2$ is used as the guest molecules and the hydrate thereof is produced in the voids of the layer.

In accordance with the method for substitution of gas hydrate of the present invention, it is possible to substitute the gas hydrate without causing weakening or collapse of the layer. This is because, only by injecting the emulsion where the minute particles of the second guest molecules are admixed with seawater into the layer where the hydrate of the first guest molecules exists, the decomposition of the gas hydrate in which the first guest molecules have been included can be progressed at a rapid reaction rate while a gas hydrate in which the second guest molecules are included is produced. Therefore—even if a submarine landslide on a large scale were to occur as a result of an earthquake or the like—during the operation for the gas hydrate substitution, there would not be much risk of leaking of the gas of the second guest molecules which is injected into the layer. Nor would there be much risk of leaking of the gas of the first guest molecules which is produced by the decomposition into the atmosphere. Nor would there be much risk of the release of the gas hydrate into the atmosphere as a result of ascending the gas hydrate with buoyancy and then allowing it to gasify. In addition, since the reaction area necessitated for accelerating the chemical reaction is enlarged by making the second guest molecules into the minute particles and thus the heat necessitated for decomposing the gas hydrate can be supplied efficiently by the heat on the production of the other gas hydrate, it is possible to repress the generation of $CO_2$ for obtaining the heat.

Further, in accordance with the method for substitution of gas hydrate of the present invention, it is possible to control the rise in temperature of the layer in order to regulate the decomposition rate of the gas hydrate to be substituted, when the mixing ratio of the liquid of the guest molecules and water in the emulsion is varied so as to control the heating value per unit volume of emulsion, or when the temperature of water as the dispersion medium is varied so as to change the temperature of the emulsion in itself.

Further, according to the method for substitution of gas hydrate of the present invention, it is possible to control the production rate of the hydrate of the second guest molecules, when the specific surface area of the minute particles of the liquid of the guest molecules in the emulsion is varied by varying the size of the minute particle.

Further, in the method for substitution of gas hydrate of the present invention, it is possible to fixate a great amount of $CO_2$—which is the cause of global warming—on the ground in the form of a stable hydrate into the layer, while collecting the $CH_4$ in marine sediments by utilizing the heat of reaction for the hydrate production, when the first guest molecules are $CH_4$ and the second guest molecules are $CO_2$.

In accordance with the method for mining of gas hydrate of the present invention, it is possible to fixate a great amount of $CO_2$—which is the cause of global warming—on the ground in the form of a stable hydrate into the layer at a high reaction rate, while collecting the $CH_4$ in marine sediments by utilizing the heat of reaction for the hydrate production, when the first guest molecules are $CH_4$ and the second guest molecules are $CO_2$. Further—since the mining of the $CH_4$ hydrate is progressed while substituting the $CH_4$ hydrate with the $CO_2$ hydrate—there is no danger of causing the weakening or collapse of the layer. In addition, since the energy for decomposing the $CH_4$ hydrate is obtained by using the $CO_2$—which is fixate as waste in the layer—as a heating agent. Therefore, it is possible to give the additional value to the waste $CO_2$ and to utilize the energy effectively.

Further, in accordance with the method for mining of gas hydrate of the present invention—since the seal layer of $CO_2$ hydrate is formed in the layer which is rested on the $CH_4$ hydrate layer as the target of mining—by the production method for gas hydrate of the present invention, the solid phases in the layer are mutually adjoined owing to the fact that the voids in the layer are filled with the $CO_2$ hydrate, and become stable. Therefore, even if a large-scale submarine landslide occurs due to an earthquake or the like, there is not much risk of a leak of $CH_4$ gas—which is produced by decomposition of the $CH_4$ hydrate—into the atmosphere, or of the release of the $CH_4$ hydrate into the atmosphere as a result of ascending the $CH_4$ hydrate with the buoyancy, wherein the density of $CH_4$ hydrate is lower than that of seawater, and then allowing it to gasify. This point is particularly useful since the ocean sedimentary layer where the $CH_4$ hydrate is deposited is accumulated in a sand layer. In addition, it is possible to fixate the $CO_2$ as a stable hydrate in both of the $CH_4$ hydrate layer and the seal layer.

Further, in accordance with the method for mining of gas hydrate of the present invention—since the seal layer of $CO_2$ hydrate is formed in the layer which is rested on the $CH_4$ hydrate layer as the target of mining, and the heating layer of $CO_2$ hydrate is formed in the layer which is rested under the $CH_4$ hydrate layer—by using the production method for gas hydrate of the present invention, it is possible to mine and recover the $CH_4$ hydrate safety without causing leak of methane gas. It is also possible to fixate a large amount of $CO_2$ as a stable hydrate into three layers, i.e., the seal layer, the layer which functions as the heating source, and the layer from which the $CH_4$ hydrate is mined.

DETAILED DESCRIPTION OF THE PREFERRED EMBODIMENTS

Figure 1:
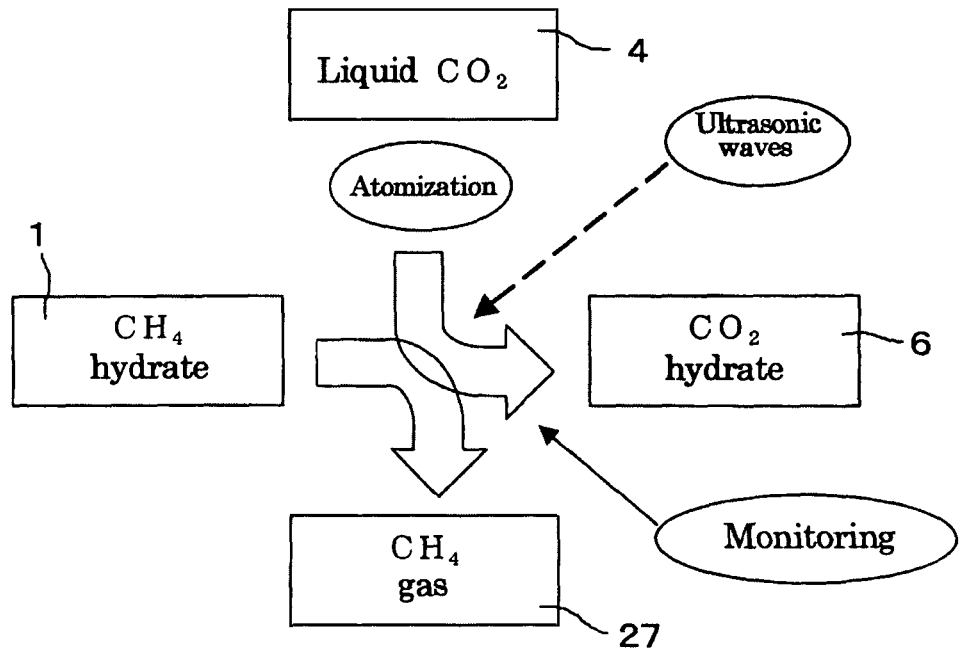
FIG. 1 is a schematic diagram which illustrates an embodiment of the present method for substitution of gas hydrate according to the present invention.

In FIGS. 1-5, an embodiment of the method for substitution of hydrate in the layer, which utilizes the method for production of gas hydrate according to the present invention, is illustrated. In the description of this embodiment, the method for production of gas hydrate will be also explained. The method for substitution of gas hydrate according to the present invention is a method wherein the production of a gas hydrate is artificially promoted in a layer, which brings the layer to a raised-temperature condition, and thereby a natural gas hydrate which has been produced in the layer is decomposed. Thus, the guest molecules are replaced. A liquid 4 of second guest molecules is injected in a form of emulsion 5, wherein the liquid 4 of second guest molecules is dispersed as particles having a size of less than the size of voids 3 in a dispersion medium 24, into the voids 3 in a layer 2 where hydrate 1 of first guest molecules exists. Wherein the second guest molecules can form hydrate under a higher temperature and lower pressure condition as compared with the temperature and pressure condition under which the first guest molecules form hydrate.

Figure 2:
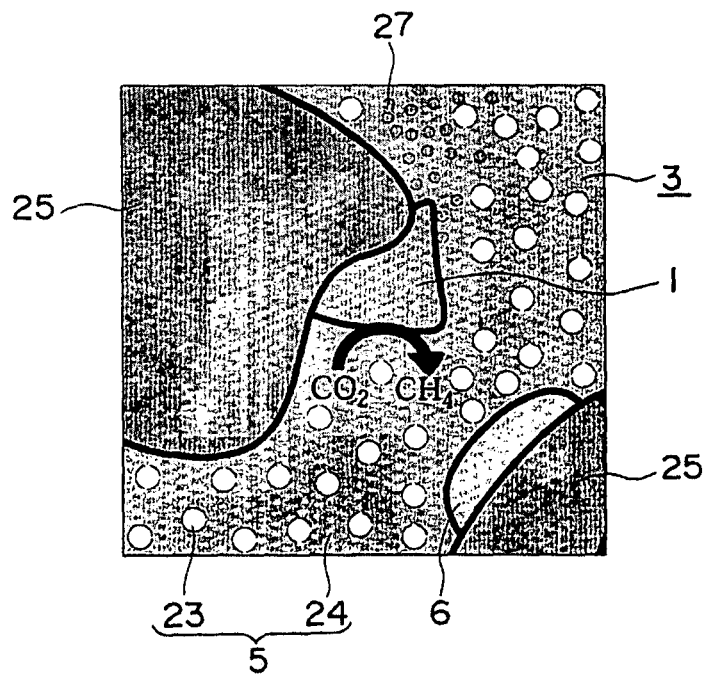
FIG. 2 is a diagram which illustrates a state of producing $CO_2$ hydrate and decomposing $CH_4$ hydrate when liquid $CO_2$ is injected into voids under the condition that the liquid $CO_2$ has been divided into minute particles.
Figure 3:
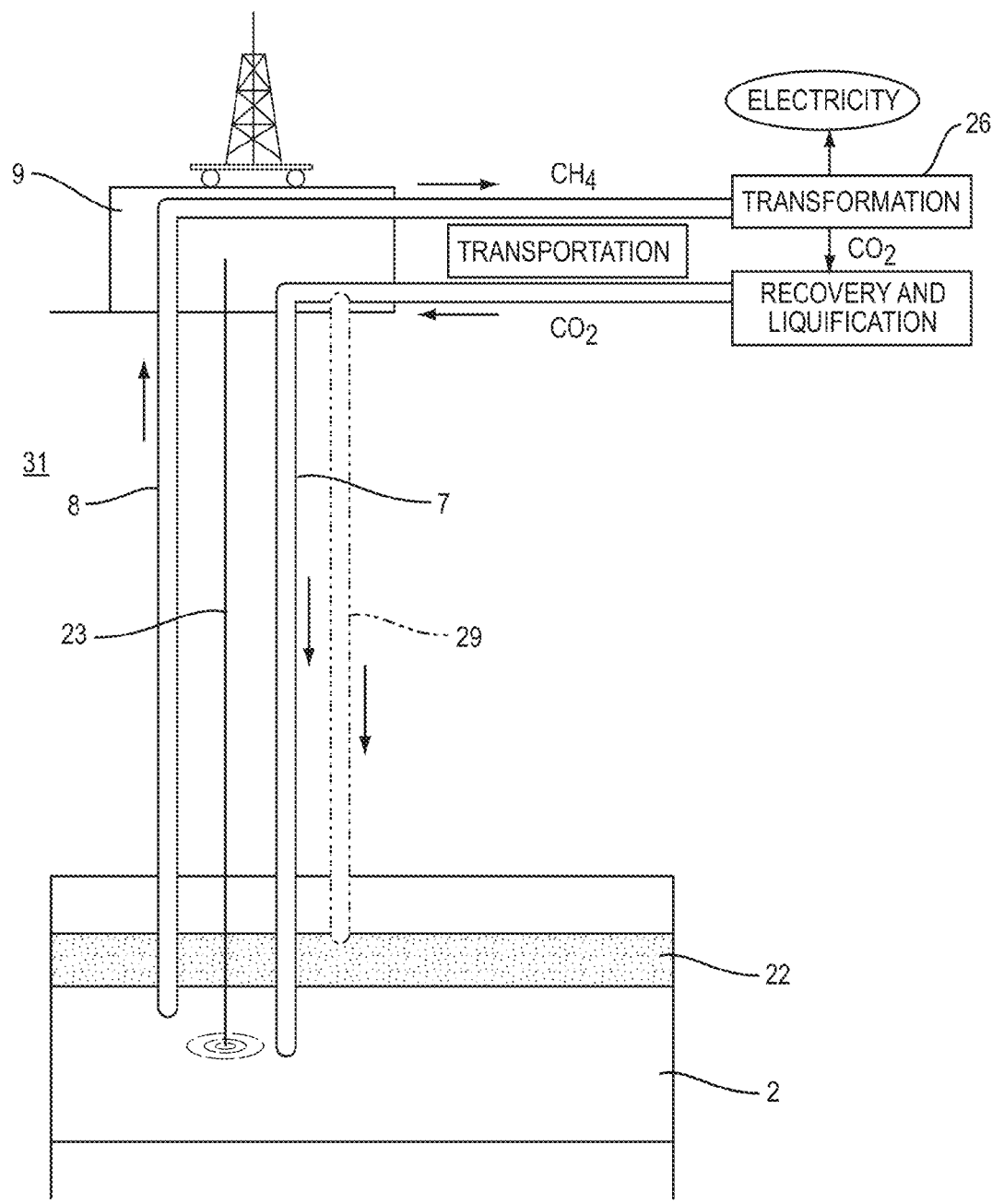
FIG. 3 is a schematic diagram which illustrates a state of substitution of $CH_4$ hydrate with $CO_2$ hydrate.

Reference numeral 25 in FIG. 2 denotes sand particles in the layer 2. The layer 2 may be, for instance, a submarine layer. Water or seawater which can form a crystal for entrapping the guest molecule is used as the dispersion medium 24 of the emulsion. Herein, the voids in the layer are spaces between solid phases (sand particles, $CO_2$ hydrate, $CH_4$ hydrate), and substantially mean regions which are occupied by liquid phase (liquid $CO_2$, water, seawater) and gas phase (methane gas). That is, the liquid of the guest molecules is spouted as the emulsion where the liquid of the guest molecules is dispersed as particles having a size of less than the size of the spaces between the solid phases in the layer where the gas hydrate is formed.

The first guest molecules in the method for substitution of gas hydrate according to this embodiment may be, for example, $CH_4$, and the hydrate 1 of the first guest molecules may be $CH_4$ hydrate. Further, the second guest molecules may be, for example, $CO_2$, the hydrate 6 of the second guest molecules may be $CO_2$ hydrate, and the liquid 4 of the second guest molecules may be liquid $CO_2$.

Figure 7:
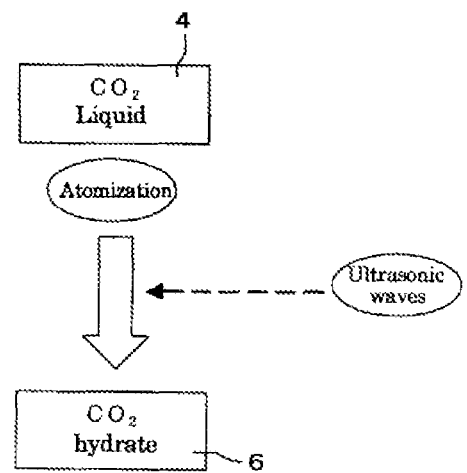
FIG. 7 is a schematic diagram which illustrates an embodiment of the method for production of gas hydrate according to the present invention.
Figure 8:
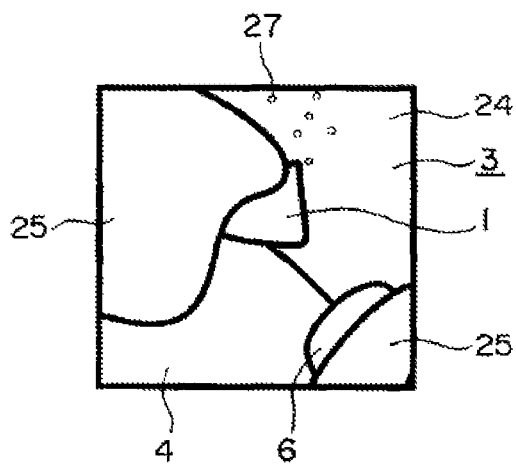
FIG. 8 is a diagram which illustrates a state of producing $CO_2$ hydrate and decomposing $CH_4$ hydrate when liquid $CO_2$ is injected into voids under the condition that the liquid $CO_2$ is not divided into minute particles.
Figure 9:
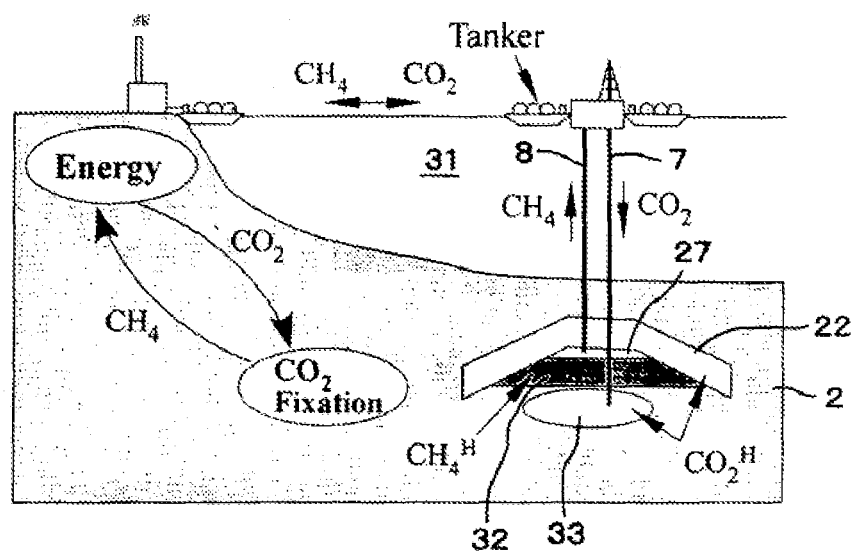
FIG. 9 is a schematic diagram which illustrates an embodiment of the method for mining of gas hydrate by showing an example for mining of $CH_4$ hydrate.

FIG. 7 is a chart showing phase equilibrium of $CH_4$ hydrate and $CO_2$ hydrate. The region below the curve A is the stable region of $CO_2$ hydrate 6, the region below the curve B is the stable region of $CH_4$ hydrate 1, the region at the left of the curve C is the region where $H_2O$ becomes solid, and the region at the right of the curve C is the region where $H_2O$ becomes liquid. As is clear from FIG. 7, assuming that the pressures are the same, the temperature at which the $CO_2$ hydrate 6 exists in stable is higher than the temperature at which the $CH_4$ hydrate 1 exists in stable. Further, assuming that the temperatures are the same, the pressure under which the $CO_2$ hydrate 6 exists in stable is lower than the pressure under which the $CH_4$ hydrate 1 exists in stable. That is, the temperature and pressure under which the $CO_2$ hydrate 6 exists in stable is higher temperature and lower pressure as compared with the temperature and pressure under which the $CH_4$ hydrate 1 exists in stable. The region surrounded by curves A, B and C is the region which temperature and pressure conditions permit causing both the production of $CO_2$ hydrate 6 and the decomposition of $CH_4$ hydrate 1 concurrently. Thus, this region may be used to substitute the $CO_2$ hydrate 6 for the $CH_4$ hydrate 1. By substituting the $CO_2$ hydrate 6 for the $CH_4$ hydrate, it becomes possible to mine $CH_4$ while fixating $CO_2$.

In submarine ground, the places where the $CH_4$ hydrate is accumulated are sand layer. Thus, the target for mining the $CH_4$ hydrate is set to such an accumulated place. It has been found that $CH_4$ hydrate exists in spaces which constitute a three-dimensional network structure occupying about 50% of the sand layer, and the $CH_4$ hydrate is, at the most, of 60% of the spaces. Thus, the following concerns the situation in which the submarine layer 2 is the target layer for mining of the $CH_4$ hydrate and for fixating the $CO_2$ hydrate. The lower end of an injection well 7 and the lower end of a production well 8 reach the layer 2 where $CH_4$ hydrate has been produced. On the sea, a platform 9 is provided, and the injection well 7 and the production well 8 are elongated downward from the platform 9 to the bottom of the sea. The upper end of the production well 8 is connected to a pump (not shown), and thus it can pump $CH_4$ gas up together with seawater which has filled the spaces in the layer 2. The $CH_4$ gas pumped up by the production well 8 may be used, for instance, for electric power generation at thermal power plant 26, after separating it from the seawater.

Figure 4:
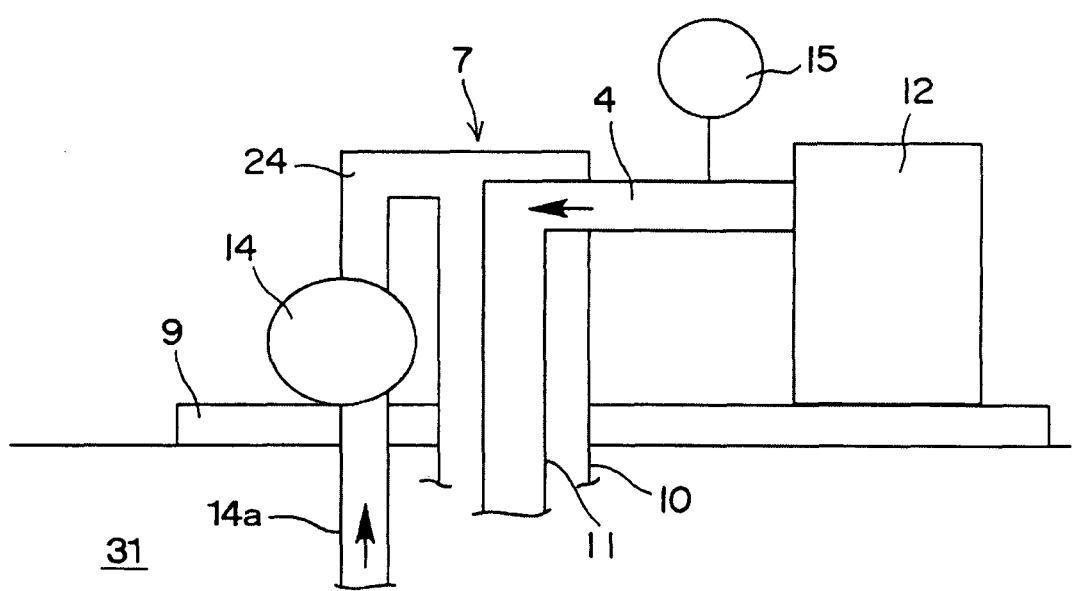
FIG. 4 is a schematic diagram which illustrates upper portions of the injection well.
Figure 5:
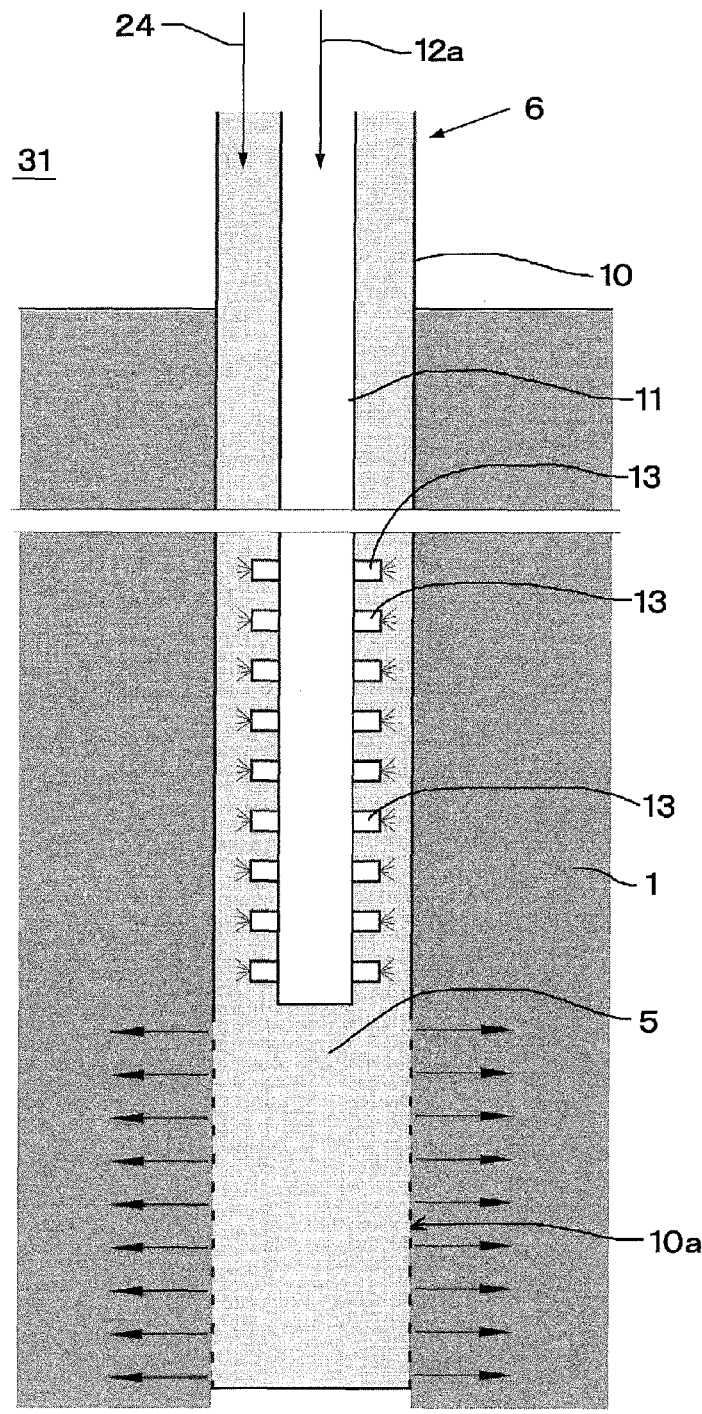
FIG. 5 is a schematic diagram which illustrates lower portions of the injection well.
Figure 6:
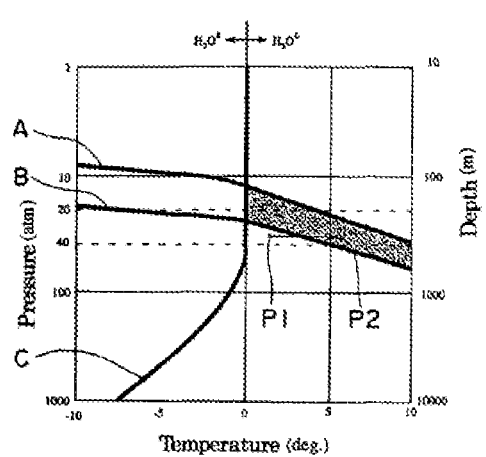
FIG. 6 is a chart showing phase equilibrium of $CH_4$ hydrate and $CO_2$ hydrate.

As shown in FIG. 4, the injection well 7 has a double pipe constitution where an inner pipe 11 is placed inside an outer pipe 10. The upper end of the inner pipe 11 is connected to a liquid $CO_2$ tank 12, and a pathway through which liquid $CO_2$ 4 flows is formed in the inner pipe 11. The liquid $CO_2$ 4 reserved in the liquid $CO_2$ tank 12 is prepared by collecting $CO_2$ discharged from the thermal power plant 26, a steelworks, or a cement plant, or the like, and liquefying the collected $CO_2$. Further, as shown in FIG. 5, at the end of the inner pipe 11, spray nozzles 13, through which the liquid $CO_2$ is sprayed as minute particles 23 which are smaller than the voids 3 in the layer 2 into the pathway which is surrounded with the outer pipe 10, are provided. By producing a high speed flows within the nozzles 13, and thus by giving shearing and collision effects, the liquid $CO_2$ can be divided into the minute particles. The method for atomization of a liquid by using nozzle, per se, is a generally known technique which is also applied in sprayers. When the pressure difference between front and rear of the nozzle 13 is set to 1 MPa to some tens MPa so that the flow rate of the liquid $CO_2$ 4 in the nozzle 13 reaches about the speed of sound, it is possible to prepare minute particles 23 of the liquid $CO_2$ 4 sprayed from the nozzle 13 in sizes on the order of less than 1 μm. Herein—since it is necessitated that the mean particle size of the minute particles 23 of liquid $CO_2$ on the spraying should be smaller than the voids in the layer where the gas hydrate is produced, i.e., the voids between the solid phases, for instance—it is preferable to be up to about 30 μm. When satisfying this condition, it is to be considered that the minute particles come to be amply smaller than the voids in the layer where the gas hydrate is produced. At a position near the liquid $CO_2$ tank 12, the inner pipe 11 is equipped with a pressure gauge 15 for measuring the pressure of the liquid $CO_2$ 4.

The upper end of the outer pipe 10 is connected to an outlet of a pump 14 which pumps seawater 24 up from the ocean 31 and discharges it, and a pathway through which the seawater 24 flows is formed at the space between the outer pipe 10 and the inner pipe 11. When the minute particles 23 of the liquid $CO_2$ 4 are sprayed into the flow of the seawater which passes through the space between the outer pipe 10 and the inner pipe 11, it is possible to prepare a $CO_2$-water emulsion 5 where the liquid $CO_2$ 4 is dispersed, as minute particles having a size of less than the voids 3, in the seawater, just before the emulsion is jetted into the layer 2. The pumping up of the seawater from the ocean 31 can be performed from any depth until reaching the sea bottom, by adjusting the length of a suction pipe 14a. The outer pipe 10 may be, for instance, a drill rod having multiple injection ports 10a for injecting uniformly the prepared $CO_2$-water emulsion 5 into the layer 2, on the peripheral surface. Injection port 10a is positioned ahead of the end of the inner pipe 11 where the spray nozzles 13 are provided.

Thereby, in the injection well 7, the weight ratio of water and $CO_2$ in the emulsion can be adjusted to a preferable value in accordance with the purpose of producing hydrate, before the emulsion is injected into the layer 2. In fact, the mixing ratio of water and $CO_2$ can be adjusted in accordance with a number of purposes, such as producing hydrate, to fixate guest molecules stably by producing hydrate in the targeted layer 2, to substitute supplied guest molecules for other guest molecules of the gas hydrate which exists in the layer, to utilize the heat of reaction obtained when the hydrate is produced as a heat source for mining a natural resource which exists in the form of hydrate in the layer, and so on. For example, as in this embodiment, in the case that $CO_2$ is fixated in the form of hydrate in the layer 2 where $CH_4$ hydrate has been accumulated, while the $CH_4$ hydrate is decomposed into water and $CH_4$ in order to collect them (thereby the $CH_4$ hydrate is mined by substituting the $CO_2$ hydrate for the $CH_4$ hydrate in the layer), it is preferable to adjust the weight ratio of water and $CO_2$ to a value suitable for the production and stability of $CO_2$ hydrate. Further, when regulating the temperature of the seawater or water used as dispersion medium of the emulsion 5, or the temperature of the liquid $CO_2$, it is possible to inject the emulsion at a temperature condition which is profitable for producing the hydrate and maintain it stably against the temperature condition of the layer and the temperature rising condition of the layer. For instance, when varying the depth for collecting the seawater, it is possible to obtain water or seawater at a desired temperature with ease.

The emulsion 5 jetted from the injection well 7 enters into voids 3 of the $CH_4$ hydrate layer 2, while displacing seawater which have been filled in the voids, and thus the liquid $CO_2$ and the seawater can reach every part of the voids 3 with a uniform ratio. In the voids, $CH_4$ hydrate is in existence stably. Thus, the temperature and pressure condition of the voids 3 is also to be a temperature and pressure condition where the $CO_2$ hydrate can exist stably. Therefore, $CO_2$ hydrate 6 is produced from the emulsion 5 which entered into the voids.

The production of hydrate is an exothermic reaction, whereas the decomposition of hydrate is an endothermic reaction. Due to the heat emitted when the $CO_2$ hydrate 6 is produced, the temperature of the layer 2—including surrounding solid phases and liquid phases—rises, and $CH_4$ hydrate is decomposed. For example, assuming that the temperature moves upward from the point P1 to the point P2 in FIG. 7, although the voids 3 belong to the $CO_2$ stable region in FIG. 7, the voids 3 deviate from the $CH_4$ stable region. Therefore, the $CH_4$ hydrate in the voids 3 is decomposed, whereas the $CO_2$ hydrate 6 exists stably. Thus, with respect to the hydrate capable of existing in the voids 3, the $CH_4$ hydrate is replaced with the $CO_2$ hydrate. With respect to the substitution in the voids 3, the main phenomenon thereof is that the $CH_4$ hydrate 1 is decomposed following the progress of the production of the $CO_2$ hydrate—a phenomenon where the $CH_4$ that is the guest molecules of $CH_4$ hydrate 1 is replaced with $CO_2$ without causing the decomposition of the $CH_4$ hydrate 1—also occurs in a part.

Since the heat emitted when the $CO_2$ hydrate 6 is produced is absorbed on the decomposition of the $CH_4$ hydrate 1, the temperature of the voids 3 and the temperature of the layer 2 does not rise to a level that exceeds the temperature at which the $CO_2$ hydrate can be produced and can exist stably. Thus, the produced $CO_2$ hydrate 6 exists stably.

By the decomposition of the $CH_4$ hydrate 1, $CH_4$ gas 27 is generated. The $CH_4$ gas 27 forms bubbles, and they float in the seawater which flows in the void 3. Further, a part of the $CH_4$ gas 27 is dissolved in groundwater. On the other hand, since the emulsion 5 is discharged from the injection well 7 and the groundwater is pumped up by the production well 8, a flow of the groundwater from the injection well 7 to the production well 8 is formed in the voids 3. Thus, both of the bubbles of the generated $CH_4$ gas 27 and the $CH_4$ gas 27 dissolved in the seawater are collected along with the seawater by the production well 8.

As mentioned above, when the hydrate is produced by injecting $CO_2$ into the submarine layer, and the $CH_4$ hydrate 1 in the submarine layer which is an effectual resource is decomposed (due to the temperature rising of the layer 2 which is induced by the heat of reaction which is emitted when the $CO_2$ hydrate 6 is produced). Thereby the $CH_4$ hydrate 1 is replaced with the $CO_2$ hydrate. So, it is possible to progress the fixation of $CO_2$ and the mining of the $CH_4$ hydrate 1, as well as the recovery and stabilization of the strength of the layer, simultaneously. Further, it is also possible to use the guest molecules simply as a heating agent, such as $CO_2$ in this embodiment, which is to be fixated through the production of hydrate.

Since the liquid $CO_2$ in the emulsion 5 is brought into the form of minute particles 23 which are smaller than the voids 3 in the layer 2, the liquid $CO_2$ can enter into the voids 3 in the layer 2 with ease and without impediments to its movement, like water. Thus, it can be dispersed within the voids with a uniform distribution. Therefore, it is possible to disperse the liquid $CO_2$ uniformly over a broader region of the voids 3 in the layer 2, with a water-$CO_2$ ratio which is suitable or nearly suitable to the hydrate production. Thus, it is possible to produce the $CO_2$ hydrate uniformly over a broad region.

Further, since the liquid $CO_2$ 4 is brought into the form of minute particles, the contacting area between the liquid $CO_2$ 4 and the seawater becomes large. For instance, assuming that the particle of liquid $CO_2$ is a sphere, and its radius is one-tenth. In this assumption, the number of particles per unit volume will become 1000 times, the surface area of each individual particle 23 will become one hundredth, and the total of the surface areas per unit volume will become ten times. For instance—assuming that the surface area of the minute particle 23 when its radius is 1 mm is a criterion—when the diameter of the minute particles 23 is set to 0.01 mm or 0.001 mm, the total of the surface areas per unit volume will become 100 times, or 1000 times, respectively. As described above, since it is possible to enhance the contacting area between the liquid $CO_2$ 4 and the seawater, it becomes possible to accelerate the reaction rate so that the $CO_2$ hydrate is promptly produced.

Figure 10:
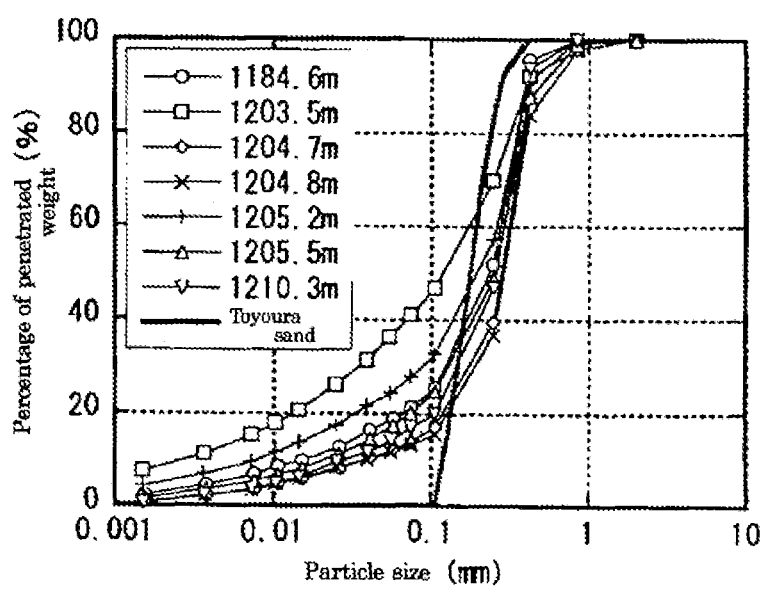
FIG. 10 is a graph which shows a distribution of particle sizes at a sedimentary layer in a Nankai trough.

For reference purposes, in FIG. 10, a state when liquid $CO_2$ 4 of almost 100% concentration is injected into voids 3 in the layer 2 under the condition that the liquid $CO_2$ are not divided into minute particles is shown. In this case, since the liquid $CO_2$ enters into the voids while the liquid $CO_2$ puts the seawater filled in the voids away from the void, the liquid $CO_2$ makes contact with the seawater only on the border between the liquid $CO_2$ and seawater. Thus, only one of the liquid $CO_2$ and seawater exists inside the border. Therefore, it is hardly possible to distribute the water and liquid $CO_2$ uniformly with a ratio which is suitable to the hydrate production in the voids 3.

Further, in accordance with the present invention, since it is possible to accelerate the production rate of the gas hydrate, the present invention is useful for not only the substitution of one hydrate for another hydrate and the mining of the resource hydrate, but also for the fixation and storage of guest molecules in hydrate form into a layer. For instance, the present invention is suitable for a technique involving fixation of $CO_2$ which has been discharged in large amount.

Further, in the present invention, since the liquid $CO_2$ is brought into the form of minute particles which are smaller than the voids in the layer 2 in advance—and thus it is supplied in emulsion form—it becomes possible to control the heating value per unit volume of emulsion 5 when the mixing ratio of the liquid $CO_2$ 4 and water in the emulsion which is injected into the voids 3 of the $CH_4$ hydrate layer 2 from the injection well 7. For example, by regulating the ratio of the liquid $CO_2$ 4 flow rate and the seawater flow rate in the injection well 7, the mixing ratio of the liquid $CO_2$ 4 and water can be varied. Thus it becomes possible to control the heating value per unit volume of emulsion 5.

The ratio of the number of guest molecules and the number of water molecules for constituting a hydrate depends on the kind of guest molecule. When the mixing ratio of the liquid $CO_2$ 4 and water in the emulsion 5 approaches the ratio of the number of $CO_2$ molecule and the number of water molecule for constituting the $CO_2$ hydrate, the quantity of the hydrate production per unit amount of the emulsion 5 increases and the heating value also increases. Conversely, when the mixing ratio of the liquid $CO_2$ 4 and water in the emulsion 5 is away from the ratio of the number of $CO_2$ molecule and the number of water molecule for constituting the $CO_2$ hydrate, the quantity of the hydrate production per unit amount of the emulsion 5 decreases and the heating value also decreases. Therefore, by varying the mixing ratio of the liquid $CO_2$ 4 and water 24 in the emulsion 5, the heating value per unit volume of emulsion 5 on the production of the $CO_2$ hydrate can be controlled. Further, by controlling the heating value per unit volume of emulsion 5 on the production of the $CO_2$ hydrate, the temperature rising of the layer 2 can be regulated. Owing to this temperature regulation of the layer 2, it becomes possible to keep the temperature of the layer 2 to the temperature capable of producing the gas hydrate, or to regulate the decomposition rate of the hydrate to be replaced or to be mined, such as $CH_4$ hydrate 1. Of course, in the cases of the replacement of $CH_4$ hydrate by the $CO_2$ hydrate production and the mining of $CH_4$ hydrate by the $CO_2$ hydrate production, the temperature regulation is not necessitated became the heating value and the endothermic heating value of both hydrates can balance each other out.

Further, in the present invention, the production rate of the $CO_2$ hydrate is controlled by varying the particle size of the minute particles 23 of the liquid $CO_2$ 4 in the emulsion 5 which is to be injected into the voids 3 of the $CH_4$ hydrate layer 2 from the injection well 7. For instance, by replacing a nozzle 13 of the injection well 3 with another one, the particle size of the minute particles 23 of the liquid $CO_2$ in the emulsion 5 can be varied. Thus, the production rate of the $CO_2$ hydrate can be controlled.

When the particle size of the minute particles 23 of the liquid $CO_2$ in the emulsion 5 becomes small, the surface area of the liquid $CO_2$ per unit volume of the liquid $CO_2$, in other words, the contacting area between the liquid $CO_2$ and the seawater increases. Thus, the production rate of the $CO_2$ hydrate increases. Conversely, when the particle size of the minute particles 23 of the liquid $CO_2$ in the emulsion 5 becomes large, the contacting area between the liquid $CO_2$ and the seawater decreases. Thus, the production rate of the $CO_2$ hydrate decreases. Thus, by varying the particle size of the minute particles 23 of the liquid $CO_2$, the production rate of the $CO_2$ hydrate can be controlled.

In the case of mining the gas hydrate, it is preferable to form—on the gas hydrate layer as the target for mining—a seal layer of a gas hydrate which is stable even at a high temperature and a low pressure as compared with the gas hydrate to be mined, in advance of the mining. For instance, in the case of mining $CH_4$ hydrate in this embodiment, the substitution of hydrate is done after the seal layer 22 of the $CO_2$ hydrate is formed onto the $CH_4$ hydrate layer 2. Since $CO_2$ can present stably in the form of hydrate even at a higher temperature and lower pressure condition—as compared with $CH_4$—$CO_2$ is preferable as the seal layer 22 to be formed onto the $CH_4$ hydrate layer 2. First, by providing a injection well 29 which penetrates into a layer which is located on the $CH_4$ hydrate layer 2 of which temperature and pressure condition allows $CO_2$ to form its hydrate, and injecting the $CO_2$-water emulsion 5 through the infusing well 29 into the voids 3 between the solid particles in the layer—wherein the $CO_2$-water emulsion 5 is maintained under such conditions that liquid $CO_2$ is dispersed in the seawater in the form of minute particles smaller than the voids 3—the seal layer 22 is formed. Thereafter, by injecting the above mentioned $CO_2$-water emulsion 5 into the voids 3 between the solid particles the $CH_4$ hydrate layer 2, the $CO_2$ hydrate is produced therein. Meanwhile, the $CH_4$ hydrate present in the voids 3 is decomposed by utilizing the heat of reaction for the $CO_2$ hydrate production. The $CH_4$ gas 27 produced by the decomposition of the $CH_4$ hydrate is entrapped by the seal layer 22, so as to be able to be collected through the production well 8 without leaking out to the sea or the atmosphere. Thus, the $CH_4$ hydrate embedded in the layer can be recovered as $CH_4$ gas while it is replaced with the $CO_2$ hydrate.

In the situation in which the seal layer 22 is formed by the production of gas hydrate—but it is formed at a layer where a natural gas hydrate is not embedded, it may be necessary to regulate temperature so as to attain the temperature capable of producing the gas hydrate which forms the seal layer 22 because the endothermic heat due to the decomposition of the gas hydrate can not be expected. This regulation may be accomplished, for instance, by regulating the temperature of the emulsion 5 or regulating the mean diameter of the minute particles of the liquid guest molecules. For example, in the situation in which the guest molecules are $CO_2$, depending on the circumstances, it may be necessary to make certain adjustments. For example, the volume of the seawater to be mixed with the minute particles 23 of the liquid $CO_2$ in the $CO_2$-water emulsion may be increased. Alternatively, the temperature of the seawater to be mixed may be set to a lower temperature. Separately, it is also possible to repress the heating value per unit volume of the emulsion 5 by varying the mixing ratio of the liquid $CO_2$ and water in the emulsion. Further, it is also possible to regulate the production rate of the $CO_2$ hydrate by varying the particle size of the minute particles of the liquid $CO_2$ in the emulsion 5.

Figure 11:
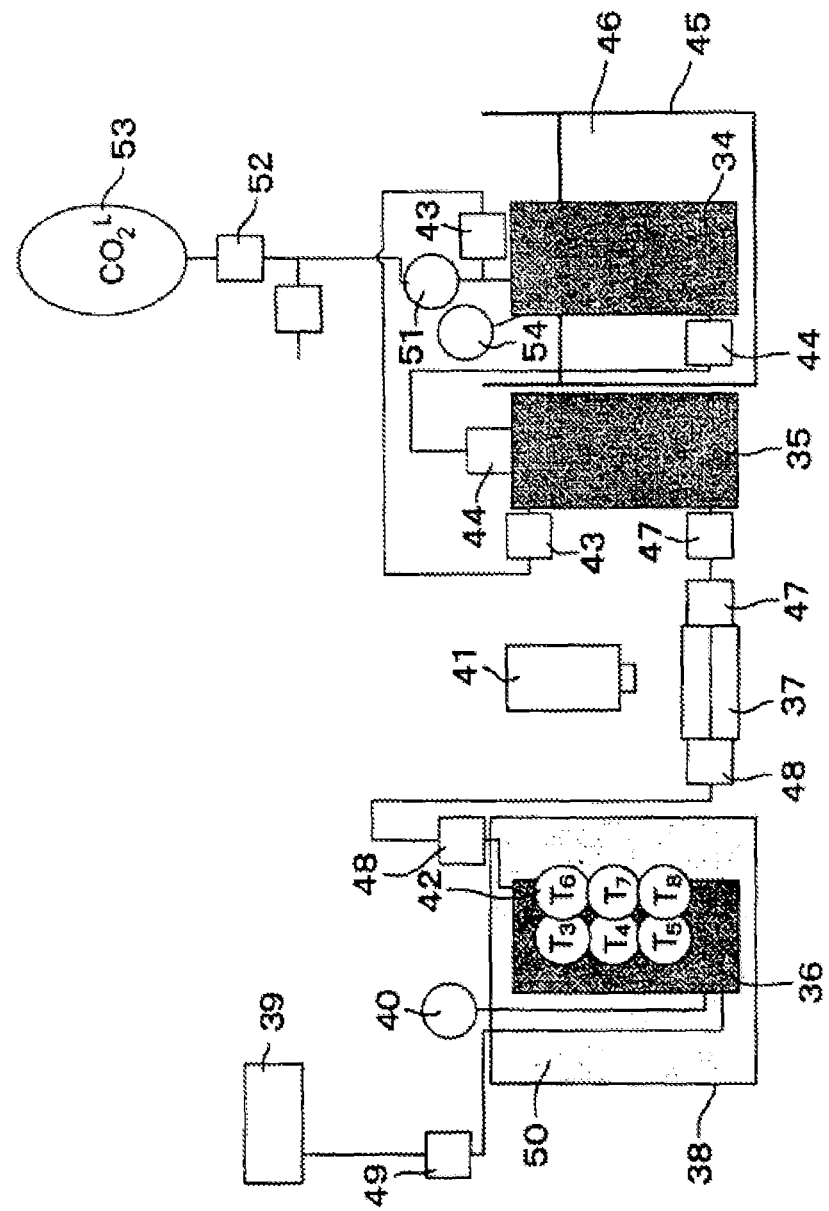
FIG. 11 is a schematic diagram of an experimental device.

Next, an embodiment of another method for mining of the gas hydrate is shown in FIG. 11. In this method for mining the gas hydrate, first, a dome-shaped seal layer 22 of the $CO_2$ hydrate is formed on a $CH_4$ hydrate layer 32 as the target to be mined. A $CO_2$ hydrate layer 33, in order to fixate the $CO_2$ hydrate, is formed at a layer which is rested under the $CH_4$ hydrate layer 32. Then, the temperature of this layer 33 into which the $CO_2$ emulsion is injected is raised by heat of reaction in the $CO_2$ hydrate production. By the raise in temperature, the $CH_4$ hydrate existing in the $CH_4$ hydrate layer 32 which is resting on this layer 33 is decomposed into water and $CH_4$ gas from the lower side. The $CH_4$ gas 27 generated by the decomposition of the $CH_4$ hydrate layer 32 is collected by the dome-shaped seal layer 22 temporarily, and then it is recovered through the production well 8 to the ground. In addition, into the layer after mining the $CH_4$ hydrate, the $CO_2$-water emulsion is injected by an operation of moving the injection well 7 upward. Alternatively, another injection well may be provided which penetrates into the $CH_4$ hydrate layer 32, in order to produce the $CO_2$ hydrate therein. Thereby, solid phases such as sand particles, which have been brought into a mutually unconsolidated condition, can be consolidated by the $CO_2$ hydrate. Thus, the strength of the layer can be restored. Therefore, it is possible to fixate a large amount of $CO_2$ in the form of stable hydrate as the three layers 22, 32, and 33 into the submarine layer. Incidentally, the region over the $CH_4$ hydrate layer 32 is stabilized by producing the $CO_2$ hydrate which forms the seal layer 22 and by which the solid phases in this layer are consolidated in advance of mining the $CH_4$ hydrate Therefore, even if a submarine landslide on a large scale will happen due to an earthquake or the like, there is no great risk of a leak of the $CH_4$ gas obtained by the decomposition of the $CH_4$ hydrate into the atmosphere. Nor is there much risk of a release of the $CH_4$ hydrate which has a lower density than the seawater into the atmosphere as a result of an ascent of the $CH_4$ hydrate.

Although the above mentioned embodiments are preferable embodiments of the present invention, many and various changes or modifications can be made without deviating from the spirit and scope of the present invention. Although the present invention is described by exemplifying the fixation of $CO_2$ by hydration, the substitution of $CO_2$ hydrate with $CH_4$ hydrate, and the mining of $CH_4$ hydrate in the above mentioned embodiments, the guest molecules to be targeted is not limited thereto. It will be clearly understood that the present invention can be applied to all guest molecules which can form a gas hydrate. With respect to the substitution of the hydrate, it can be also applied to any combinations of two guest molecules which are different from each other regarding the temperature and pressure condition for stably existing in their hydrate forms. For example, as the guest molecules of natural gas hydrate, methane ($CH_4$), ethane ($C_2H_6$), propane ($CH_3CH_2CH_3$), carbon dioxide ($CO_2$), hydrogen sulfide ($H_2S$), air (nitrogen, $N_2$) are known. It will be clearly understood that the methods according to the present invention can be applied to the production, substitution, and mining of the gas hydrate of these guest molecules.

Further, although in the abovementioned-embodiment, the methods for production, substitution, and mining of the gas hydrate in the submarine layer which mainly comprises the sand layer are described, the present invention can be applied to the layer such as $CH_4$ hydrate layer below a lake bottom, $CH_4$ hydrate layer of a permafrost, etc. Further, in the present invention, the guest molecules are injected in the voids in the layer, in the form of emulsion 5. Wherein the emulsion 5 includes water necessitated for the production of hydrate. Therefore it is possible to perform the fixation, the substitution, and the mining owing to the production of the hydrate of the guest molecules, aimed at a layer whose voids lack water.

In addition, depending on the status of the layer, water/seawater may be sprayed into the liquid $CO_2$ by flowing the liquid $CO_2$ through the outer pipe 10 and flowing the water/seawater the inner pipe 11 in order to adjust the ratio of the liquid $CO_2$ and the water/seawater in emulsion 5. Further, although in the above-mentioned embodiments the emulsion is prepared by injecting the liquid $CO_2$ into the water/seawater in advance of injecting the emulsion into the layer, it is also possible to inject the liquid $CO_2$ directly from a spray nozzle into the layer where the $CH_4$ hydrate exists. This will disperse the liquid $CO_2$ as minute particles into the seawater, or the like, in the layer and form the emulsion. Thereafter, it will serve to diffuse the emulsion into the layer by utilization of the energy provided by the injection.

EXAMPLES

Example 1

Laboratory experimentation was performed in order to confirm whether the diameters of minute particles of the liquid $CO_2$ which are suspended in the $CO_2$-water emulsion can be made to be smaller than the size of voids in a sedimentary layer (voids between solid phases). Initial experimentation was conducted with respect to a sand layer in the Nankai trough which is a promising target for mining of the $CH_4$ hydrate. This sand layer in the Nankai trough includes clay (particle size: 0.005-0.001 mm) and silt (particle size: 0.075-0.005 mm) at about 20%. The percentages of penetrated weight thereof were shown in FIG. 12. The sample of the sand layer in the Nankai trough had been obtained by trial diggings presided by Ministry of Economy, Trade and Industry of Japan. Further, experimentation was conducted by the inventors hereof using Toyoura sand in the range of 0.1-0.6 mm which was adjusted to the percentage of penetrated weight shown in FIG. 12 as an indicator for their lab experiment. The atomization of the liquid $CO_2$ was accomplished by using a typical spray nozzle known to those of skill in the art. When spraying water from this nozzle under normal temperature and normal pressure and by setting the inner pressure to 1 MPa, the diameter of water drops was in the range of 30-40 µm. However, the spraying condition for the liquid $CO_2$ was unknown. Thus, assuming that the condition for the liquid $CO_2$ would adhere to that for the water, the differential pressure between a pressure vessel 34 into which the liquid $CO_2$ was charged and an atomizing pressure vessel 35 on which the nozzle was provided was set to 1 MPa, with respect to the spraying pressure.

Figure 13:
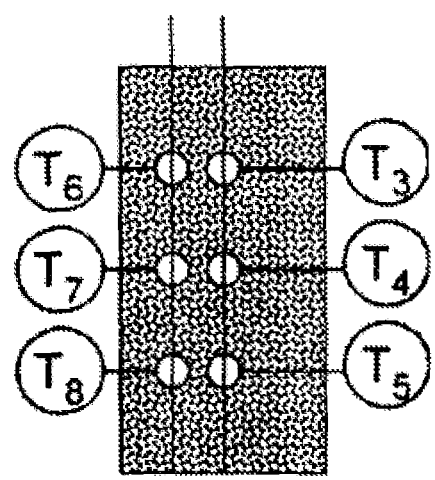
FIG. 13 is a schematic diagram which shows positions for measuring temperature in a pressure vessel for producing $CO_2$ hydrate.

The experimentation was conducted by using the experimental instrument as shown in the schematic diagram of FIG. 13. Three pressure vessels, i.e., the liquid $CO_2$ pressure vessel 34, the liquid $CO_2$ atomizing pressure vessel 35, and a microscopic observing pressure vessel 37, which were mutually connected by pipe lines, constituted the experimental instrument. Into the liquid $CO_2$ pressure vessel 34, $CO_2$ was injected at the room temperature, so that the $CO_2$ gas was charged over the liquid $CO_2$ layer. Into the liquid $CO_2$ atomizing pressure vessel 35, water was injected, and then the $CO_2$ gas was charged over the water. Incidentally, in this figure, numerals 45, 46, 51, 52, 53, 54 denote a water tank, hot-water, a pump, a valve, and a tank for liquid $CO_2$, and a thermometer, respectively. Numerals 40, 41 and 49 represent a pressure gauge, a microscope and valve, respectively.

Into the liquid $CO_2$ pressure vessel 34, carbon dioxide—which had been liquidized under an initial condition that the temperature was 19° C. (room temperature) and the pressure was 5.2 MPa—was sealed. Then it was warmed in hot water. When the temperature and the pressure reached 25° C. and 6.2 MPa, respectively, the valve 44 was opened to supply the liquid $CO_2$ to the atomizing pressure vessel 35. In the atomizing pressure vessel 35, the liquid $CO_2$ was sprayed through the spray nozzle (not shown) toward the $CO_2$ gas as an upper layer in the atomizing pressure vessel 35, and then the minute particles of the liquid $CO_2$, fell into the water layer as an lower layer in the pressure vessel 35 which was stirring with a stirrer. Thus, the $CO_2$-water emulsion was prepared. Incidentally, before the warming in hot water, the inner pressure in the liquid $CO_2$ pressure vessel 34 and the inner pressure in the atomizing pressure vessel 35 were equalized by opening the valve 43.

Figure 12:
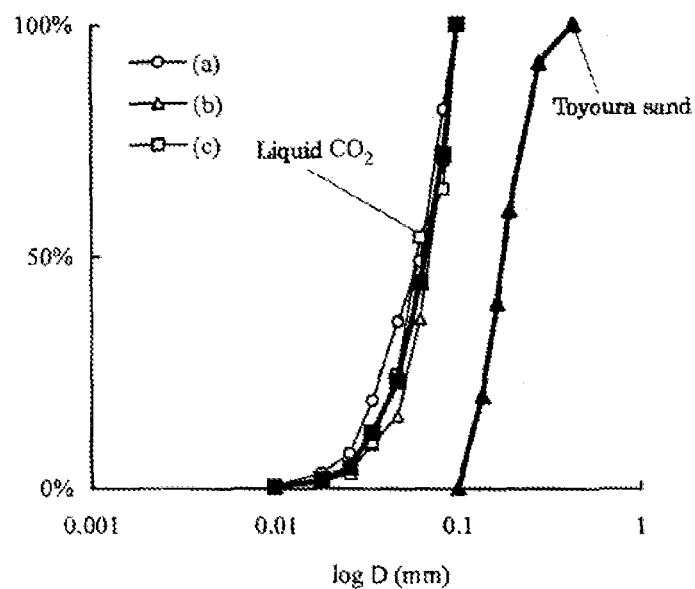
FIG. 12 is a graph which shows the relationship between particle size and percentage of penetrated weight with respect to the finely divided liquid $CO_2$ in water and Toyoura sand.

Thereafter, the $CO_2$-water emulsion were introduced into the microscopic observing pressure vessel 37 by opening the valve 47, and the microscopic observation was conducted. The $CO_2$-water emulsion in the sampling room which was formed between pressure-proof glasses of 10 mm in thickness of the microscopic observing pressure vessel 37 was observed by using a stereo-microscope of 60 times magnification, known to those of skill in the art. After the observation, by using the microscopic photograph the diameters and counts of minute particles at the three points (a, b, c) were examined. The relationships between the diameter and count of liquid $CO_2$ at the three points were as shown in Table 1. When the relation between the particle sizes of the liquid $CO_2$ and the percentages of penetrated weight was determined, it was found that the diameters of the liquid $CO_2$ were within the range of 10-100 μm as shown in FIG. 12. Thus, they were sufficiently smaller than the Toyoura sand (100-600 μm). In addition, it was similar in distribution to the Toyoura sand.

Judging from these results, the emulsion which includes a large volume of liquid $CO_2$ can enter into the voids between the solid phases—such as sand particles—while it directs the seawater or water filled in the voids away from the void. Namely, the $CO_2$ particles which are smaller than the voids in the layer where the gas hydrate has been produced, i.e., the voids between the solid phases—sand particles—can flow through the voids, as is the case with water.

Example 2

The behavior for the production of $CO_2$ hydrate when the $CO_2$ water emulsion (obtained in Example 1) was permeated into the Toyoura sand in the $CO_2$ hydrate-producing pressure vessel 42 (which simulated the sand layer in the ocean sedimentary layer) was observed by using, as indicators, the temperature and pressure. The schematic diagram of the experimental instrument used in the production of the $CO_2$ hydrate is shown in FIG. 13. This experimental instrument was the same as that of Example 1, except that the $CO_2$ hydrate producing pressure vessel 36 was further connected downstream from the liquid $CO_2$ atomizing pressure vessel 35. The inside of the $CO_2$ hydrate producing pressure vessel 36 was pressurized by a hand-operated pump 39 under the condition that the water was supplied into the $CO_2$ hydrate-producing pressure vessel 36 from a water tank (not shown). The $CO_2$ hydrate-producing pressure vessel 36 was charged with the Toyoura sand and water which simulated the sand layer in the ocean sedimentary layer, the sand layer being within the range of the particle diameters shown in FIG. 12, so as to satisfy a porosity of about 50%. Incidentally, in this experiment, since there is no necessity to confirm the condition of the $CO_2$-water emulsion, the $CO_2$ hydrate producing pressure vessel 36 may be connected directly to the liquid $CO_2$ atomizing pressure vessel 35 in the downstream of the pressure vessel 35. The numeral 45 represents a pressure gauge.

First, to, the $CO_2$ hydrate producing pressure vessel 36—which had been charged with 314.09 g of the Toyoura sand saturated with 79.47 g of water and which had been pressurized up to about 5 MPa by using the hand-operated pump—39, 30.78 g of the $CO_2$-water emulsion were introduced from the upside of the pressure vessel 36. This was done under the condition that a valve which was located at the downside of the pressure vessel 36 was slightly opened to an extent that the pressure inside the pressure vessel 36 was not decreased, so that the water existing in the voids were extruded from the pressure vessel 36 by the emulsion and the emulsion was introduced into the pressure vessel. When the emulsion was discharged from the downside of the pressure vessel, the valve was closed. Under these conditions, the water contained in the pressure vessel was 48.69 g. Then, by utilizing the iced water 50 in the water tank 38, the pressure vessel was cooled down for two hours to a temperature that is a stable condition for the $CO_2$ hydrate, in order to produce the $CO_2$ hydrate. Incidentally, the injection of the liquid $CO_2$-water emulsion was proceeded by opening the valve 48 so as to introduce the liquid $CO_2$-water emulsion—which had been prepared in the liquid $CO_2$ atomizing pressure vessel 35—into the $CO_2$ hydrate producing pressure vessel 36. The discharge of the emulsion can be easily detected, because of the fact that the pressure falls to the atmospheric pressure which allows the minute particles of the liquid $CO_2$ in the emulsion to vaporize.

Figure 14B:
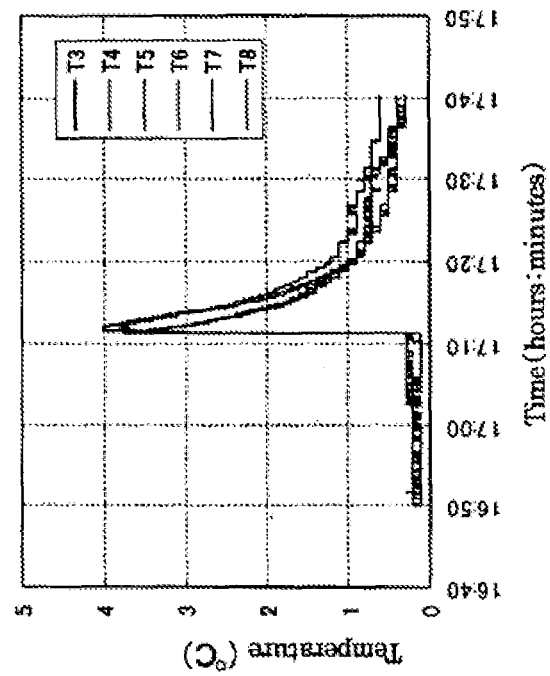
FIG. 14 is a graph which shows a result of an experiment for production of $CO_2$ hydrate, wherein (A) shows the temperature change from the start time to the end time in the experiment, and (B) shows the temperature change before and after the production of $CO_2$ hydrate in a magnified scale.
Figure 14:
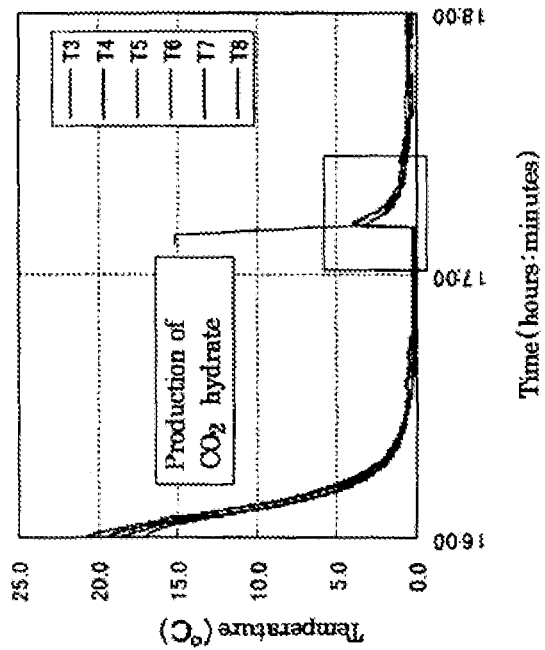
Figure 15:
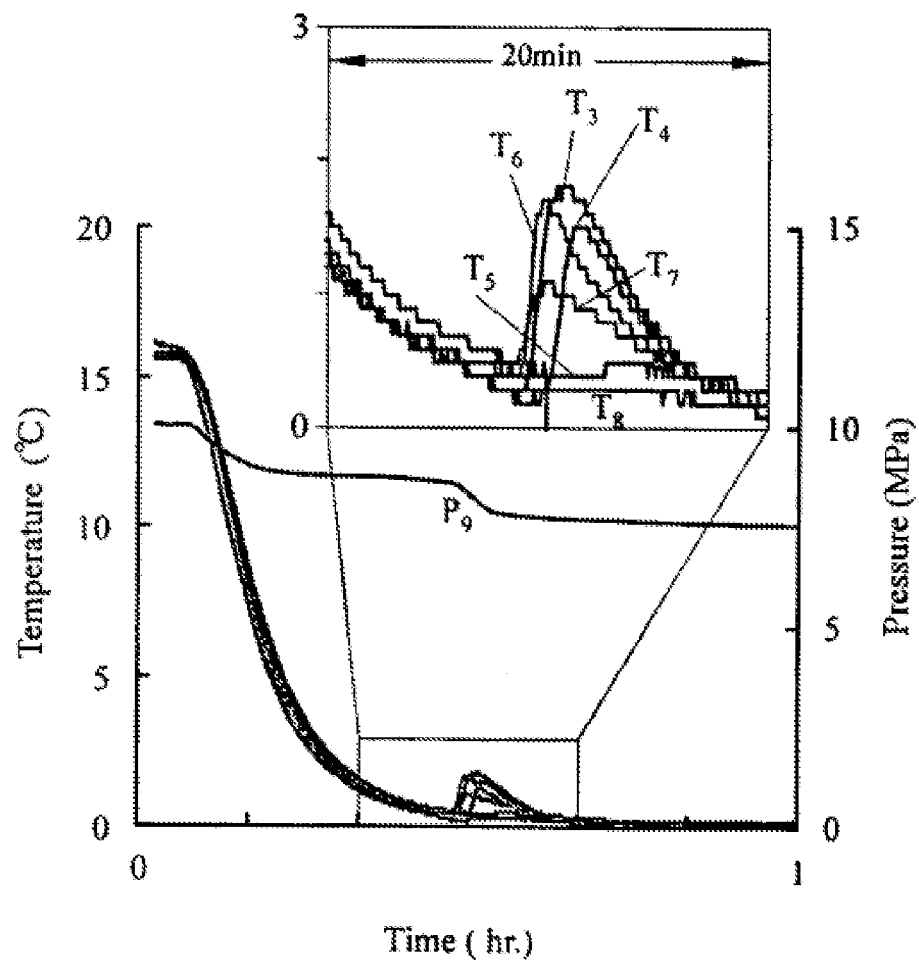
FIG. 15 is a graph which shows a result of an experiment for production of $CO_2$ hydrate as Control 1, wherein gas hydrate is produced from liquid $CO_2$.

The temperature changes in the pressure vessel 36 at that time which were measured by thermometers 42 located at the six points shown in FIG. 13, is shown in FIG. 14. According to the results of the measurements, the temperatures at the six points rose at the same time and in similar fashion. These temperature changes were considered to be due to the fact that $CO_2$ hydrate was produced uniformly. The $CO_2$ was also considered to be dispersed uniformly throughout the sample. By the way, the inner pressure of the vessel was varied within the range of 4-9 MPa.

In this experiment, the pressure vessel 36 was dipped in the iced water. Thus, this experiment was performed under conditions in which the heat could be dissipated (heat transmission). The rise in temperature at the respective measurement points T3-T8 was about 4° C. However, in the case of the actual ocean sedimentary layer, there are areas where the initial temperature is not changed. Thus, under conditions in which the initial temperature is not changed, a non-steady thermal diffusion analysis was conducted. As the result, it was found that the temperature of the sample (mixture of the Toyoura sand, water and $CO_2$), used as an indicator, was raised by about 9° C. by the heat of reaction for the $CO_2$ hydrate production. Since the theoretically-calculated maximum temperature rise of the Toyoura layer (mixture of sand, water and $CO_2$) by the heat of the reaction (absolute value) for the $CO_2$ hydrate production is about 9° C., the experimental results indicate that the environment—near conditions in which the maximum temperature rising can be produced—was preserved. Specifically, the result makes it clear that—by the atomization of and the emulsifying of the liquid $CO_2$—the ideal hydrate-producing reaction is caused. In other words, the production rate of the $CO_2$ hydrate can be accelerated, and still further, the liquid $CO_2$-water emulsion can be dispersed uniformly into the sand layer. In addition the result makes it clear that the $CO_2$ can be utilized as a heating agent for the layer where the $CH_4$ hydrate exists.

From the results of Examples 1 and 2, it can be judged that the $CO_2$ particles—which are smaller than the voids—flowed in the voids in the layer and the Toyoura sand layer, as is the case with water.

<Control 1>

Into the pressure vessel 36—which had been charged with 314.09 g of the Toyoura sand saturated with 79.47 g of water and which had been pressurized up to about 5 MPa by using the hand-operated pump 39—27.14 g of liquid $CO_2$ of which pressure had been risen to about 1 MPa by dipping into hot water were introduced, and at the same time, about 25 cc of water were drawn out from the downside of the pressure vessel 36 by using the hand-operated pump. When the liquid $CO_2$ was discharged from the downside of the pressure vessel, the valve was closed. The discharge of the liquid $CO_2$ could be easily detected because of the fact that the pressure falls to the atmospheric pressure and allows the liquid $CO_2$ to vaporize. Under these conditions, the water contained in the pressure vessel was 50.85 g. Then, by utilizing the iced water 50 in the water tank 38, the pressure vessel was cooled down for two hours to a temperature that is a stable condition for the $CO_2$ hydrate, in order to produce the $CO_2$ hydrate.

The actual measurement data of the temperature changes at the six points in the Toyoura in case is shown in FIG. 13. According to the results of the measurements, the temperature changes at the six points were caused randomly with time differences. Further, with respect to the value of the temperature rise, the values of the individual points were mutually distinct, and the values—even the maximum value—did not reach 2° C. To be sure, at the measurement point relating to the minimum temperature change, the temperature rise was hardly observed. From these results, it is believed that the liquid $CO_2$ was not dispersed uniformly into the voids in the Toyoura sand layer, and that a large variation was caused in the dispersion. Further, depending on places, the liquid $CO_2$ was not supplied. Further, since there was a variation in the values of the temperature rise at the respective measuring points—and the values of the temperature rising, per se, were low—it was shown that the reaction rate for the hydrate production was slow and the reaction was not progressed actively.

The invention claimed is:

1. A method for substitution of gas hydrates, comprising:
    injecting an emulsion into voids in a layer, the emulsion comprising drops of a liquid of second guest molecules in water, the drops of liquid of the second guest molecules being dispersed in the water as drops having a size of less than a size of the voids in the layer, wherein hydrates of first guest molecules exist in the voids in the layer and the second guest molecules form hydrates under higher temperature and lower pressure conditions as compared with temperature and pressure conditions under which the hydrates of the first guest molecules form so that the hydrate of the first guest molecules in the voids is substituted by a hydrate of the second guest molecules.

2. The method for substitution of gas hydrates according to claim 1, including controlling a heating value per unit volume of the emulsion by varying a ratio of the drops of liquid of the second guest molecules and the water in the emulsion.

3. The method for substitution of gas hydrates according to claim 1, including controlling a production rate of the hydrate of the second guest molecules by varying the size of the drops of liquid of the second guest molecules in the emulsion.

4. The method for substitution of gas hydrates according to claim 1, wherein the first guest molecules are $CH_4$, and the second guest molecules are $CO_2$.

5. A method for mining of gas hydrate, comprising:
    injecting an emulsion into voids in a $CH_4$ hydrate layer as a heating agent for decomposing the $CH_4$ hydrate in the voids to mine the $CH_4$;
    the emulsion comprising drops of liquid $CO_2$ in water, the drops of liquid $CO_2$ being dispersed in the water and having a size of less than a size of the voids in the $CH_4$ hydrate layer.

6. The method for mining of gas hydrate according to claim 5, including:
    injecting the emulsion into voids in a further layer that is rested on the $CH_4$ hydrate layer for forming a seal layer of $CO_2$ hydrate;
    the further layer being under temperature and pressure conditions under which the $CO_2$ hydrate is formed; and
    recovering $CH_4$ gas by replacing $CH_4$ hydrate with $CO_2$ hydrate.

7. A method for mining of gas hydrate, comprising:
    injecting an emulsion into voids in a layer under the ground that is rested on a $CH_4$ hydrate layer to form a seal layer of $CO_2$ hydrate;
    the emulsion comprising drops of liquid $CO_2$ in water, the drops of liquid $CO_2$ being dispersed in the water and having a size of less than a size of the voids in the layer, the layer being under temperature and pressure conditions under which $CO_2$ hydrate is formed;
    injecting the emulsion into voids in the $CH_4$ hydrate layer for decomposing $CH_4$ hydrate existing in the voids in the $CH_4$ hydrate layer into $CH_4$ gas by heat of reaction of $CO_2$ hydrate formation; and
    recovering the $CH_4$ gas at the ground by collecting the $CH_4$ gas from the seal layer.

8. A method for mining of gas hydrate, comprising:
    injecting an emulsion into voids in a first layer under the ground that is rested on a $CH_4$ hydrate layer for forming a seal layer of $CO_2$ hydrate;
    the emulsion comprising drops of liquid $CO_2$ in water, the drops of liquid $CO_2$ being dispersed in the water and having a size of less than a size of the voids in the first layer, the first layer being under temperature and pressure conditions under which the $CO_2$ hydrate is formed;
    injecting the emulsion into voids in a second layer that is rested under the $CH_4$ hydrate layer for decomposing $CH_4$ hydrate existing in the voids in the $CH_4$ hydrate layer from a lower side of the $CH_4$ hydrate layer by raising the temperature of the second layer using heat of reaction of the $CO_2$ hydrate formation;
    recovering $CH_4$ gas at the ground by collecting the $CH_4$ gas from the seal layer, the $CH_4$ gas being produced by decomposition of the $CH_4$ hydrate; and
    injecting the emulsion into the voids in the $CH_4$ hydrate layer after mining of the $CH_4$ hydrate for restoring the $CH_4$ hydrate layer after mining of the $CH_4$ hydrate by producing $CO_2$ hydrate in the voids in the $CH_4$ hydrate layer after mining of the $CH_4$ hydrate.

* * * * *